US006420160B1

(12) United States Patent
Bloch

(10) Patent No.: US 6,420,160 B1
(45) Date of Patent: Jul. 16, 2002

(54) VIRUS-LIKE PARTICLES USEFUL AS A VECTOR FOR DELIVERING NUCLEIC ACID

(75) Inventor: Marie-Aline Bloch, Lyons (FR)

(73) Assignee: Pasteur Merieux Serums et Vaccins, Lyons (FR)

( * ) Notice: Subject to any disclaimer, the term of this patent is extended or adjusted under 35 U.S.C. 154(b) by 0 days.

(21) Appl. No.: 09/194,927

(22) PCT Filed: Jun. 3, 1997

(86) PCT No.: PCT/FR97/00962

§ 371 (c)(1),
(2), (4) Date: Apr. 29, 1999

(87) PCT Pub. No.: WO97/46693

PCT Pub. Date: Dec. 11, 1997

(30) Foreign Application Priority Data

Jun. 4, 1996 (FR) ............................................ 96 07174

(51) Int. Cl.[7] ........................ A01N 63/00; A61K 39/12; C12N 15/63; C12N 7/00; C12N 7/02
(52) U.S. Cl. .................... 435/239; 435/235.1; 435/455; 424/93.2; 424/93.21; 424/93.6; 424/192.1; 424/204.1
(58) Field of Search ............................. 435/320.1, 235, 435/456, 455, 239; 424/93.2, 93.21, 93.6, 192.1, 204.1

(56) References Cited

U.S. PATENT DOCUMENTS 5,789,230 A  *  8/1998  Cotten et al. ............. 435/235.1
5,855,891 A  *  1/1999  Lowy et al. ............. 424/192.1

FOREIGN PATENT DOCUMENTS

DE         4335025      *  4/1995

OTHER PUBLICATIONS

Verma et al. Gene Therapy–Promises, Problems, and Prospects. Nature, vol. 389, pp. 239–242, Sep. 18, 1997.*

Eck et al. Gene–Based Therapy. Goodman & Gilman's The Pharmacological Basis of Therapeutics, 9th Edition, Chapter 5, pp. 77–101, 1996.*

* cited by examiner

*Primary Examiner*—Deborah J. R. Clark
*Assistant Examiner*—Shin-Lin Chen
(74) *Attorney, Agent, or Firm*—Burns, Doane, Swecker & Mathis, L.L.P.

(57) ABSTRACT

The present invention relates to the use of virus-like particles (VLP's) of papillomavirus for preparing vector pseudoviruses useful for transferring genetic material into target cells of an organism

30 Claims, No Drawings

VIRUS-LIKE PARTICLES USEFUL AS A VECTOR FOR DELIVERING NUCLEIC ACID

The subject of the invention is new vectors for delivering genetic material for use i.a. in gene therapy, in immunotherapy and as a therapeutic or prophylactic vaccine.

In vertebrates, the transfer of genetic material, regardless of its ultimate usefulness, may be achieved by various procedures which, for those most widely known, are (i) transfer by viral vectors, (ii) transfer via packaging into liposomes and the like, (iii) transfer mediated by facilitating agents such as cationic lipids, gold beads or calcium phosphate and (iv) transfer by mere injection of naked DNA, that is to say DNA lacking any other components which may interact or cooperate with the DNA in order to promote its transfer.

Each method is of general application; however, one method rather than another may appear more appropriate depending on various factors such as the type of material to be transferred, the site where it is desired to express this material, the permanent or transient nature of the expression.

For example, if it involves correcting a genetic deficiency in an individual, an integrative mode of transfer using viral vectors derived from retroviruses may be preferred.

In other cases, for example in the treatment of cancers, a transient expression targeted at the site of the tumour will be favoured. To this end, viral vectors such as vaccine vectors are particularly appropriate.

In the case of vaccinal treatments, vaccine vectors, liposomes or even naked DNA may be suitable. The latter will be preferred to retroviral vectors, in particular for preventive vaccination.

It has now been discovered that the capsids of papillomaviruses may be reconstituted in vitro, in the presence of heterologous RNA or DNA, and that this genetic material became efficiently packaged therein. Thus, the capsids, commonly called VLPs for virus-like particles, can serve as vehicle for the transfer of genetic material, with various applications.

Papillomaviruses are nonenveloped small DNA viruses with an icosahedral structure. Their genome codes for up to eight early proteins and two late proteins. Their open reading frames are classified from E1 to E7 without forgetting L1 and L2. The early (E for early) genes are associated with the viral replication and cellular transformation functions. The papillomavirus capsids consist of two proteins $L_1$ and $L_2$ (L for late proteins); $L_1$ being the major constituent. Detailed information may be found in Virology, Second Ed. by B. N. Fields, Raven Press (1990).

VLPs which mimic in every respect the capsids of native virions may be obtained by recombinant expression of either $L_1$ alone, or of $L_1+L_2$, in the vaccine system (Hagensee et al., J. Virol. (1993) 67: 315) or in the baculovirus system (Kirnbauer et al., PNAS (1992) 89: 12180; Kirnbauer et al., J. Virol. (1993) 67: 6929; Rose et al., J. Virol. (1993) 67: 1936; Le Cann et al., FEMS Microbiol. Lett. (1994) 117: 269).

Since these VLPs adopt a native conformation and react with neutralizing antibodies known to recognize conformational epitopes present in the native virions, it has already been suggested to use these VLPs as vaccines against papillomavirus infections (WO 94/5792).

Many animal species, including humans, are subject to papillomavirus infections. These infectious agents are specific for the group which they infect. Thus, it is possible to distinguish between, inter alia, bovine papillomaviruses and human papillomaviruses (HPV). In humans, different types of HPV are responsible for various diseases. Types 1, 2, 3, 4, 7, 10, and 26–29 are the cause of benign verrucas. Types 5, 8, 9, 12, 14, 15, 17, 19–25, 36, and 46–50 can induce lesions in immunologically deficient individuals. Types 6, 11, 34, 39, 41–44 and 51–55 are responsible for dysplasia or nonmalignant condyloma of the genital and respiratory mucous membranes; in rare cases, some of these types may be involved in invasive carcinomas. Finally, types 16 and 18 and, to a lesser extent, 31, 33, 35 and 45 cause epithelial dysplasia of the genital mucous membrane and are very widely associated with the majority of invasive carcinomas.

The present invention provides, for its part, noninfectious papillomavirus virus-like particles (VLPs) which comprise a capsid defining an internal space and a nucleic acid molecule contained in this internal space; the nucleic acid molecule being different from the genome of a papillomavirus at least in that it lacks all or part of the regions of the said genome coding for wild-type late proteins.

For the purposes of the present invention, the capsid is mainly made of all or part of a protein L1 or of all or part of a protein L1 and all or part of a protein L2. For the sake of simplicity, only the L1 or L2 protein will be used in the text which follows to designate the whole proteins as well as fragments thereof. It can also be expected that there will be several L1 or L2 proteins obtained from different types.

Among the HPV types from which the L1 and L2 proteins may be derived, there may be mentioned in particular types 1, 6, 10, 11, 16, 18, 31, 33, 35 or 45.

When the proteins are obtained from an HPV-16, -18, -33 or -35 or from any other HPV capable of inducing an invasive carcinoma, it is preferable that the sequence of the L1 protein in use for the purposes of the invention is identical to that of the L1 protein which is present in the papillomavirus when the latter is initially isolated from a benign lesion (e.g. condyloma acuminatum or cervical dysplasia). Indeed, it in fact appears that at the stage of a benign lesion, the papillomavirus can still freely replicate in the complete virion state, whereas at the malignant stage, this function will be impaired in the virus in particular because of a mutation which would have occurred in the ORF coding for L1. This mutation would prevent, inter alia, the formation of the capsids. The sequence of a type 16 L1 protein obtained from an HPV isolated from a condyloma is disclosed in the sequence identifier No. 2 of application WO 94/5792. It can be noted that this sequence is distinguishable from that of an L1 protein of an HPV-16 isolated from a malignant carcinoma in that the amino acid at position 202 is an amino acid other than histidine, i.e. an aspartic acid or glutamic acid residue.

As regards the L2 protein, the latter may be possibly deleted for its DNA binding site in order to promote the elimination of any trace of DNA during the purification of the components necessary for using the VLPs according to the invention. In practice, this involves suppressing or modifying one or several of the first 12 amino acids of the N-terminal end. Such L2 proteins are in particular described in WO 95/20659 and Zhou et al., J. Virol. (1994) 68: 619.

Alternatively, the capsid may consist of one or more hybrid proteins (fusion proteins) corresponding to the chimeras L1-E6, L1-E7, L2-E6, L2-E7 or to any other chimera form in which at least part of an L1 or L2 protein may exist combined with a peptide or polypeptide heterologous to L1 or L2, for example an HIV (human immunodeficiency virus) gag peptide. In order to form such hybrids, several types of association are possible in theory.

For example, it is possible to envisage combining, by a peptide bond, the N-terminal or C-terminal end of the whole L1 and L2 protein with the opposite end of the E6 or E7 protein. The same action can be expected with truncated proteins. The insertion of all or part of E6 or E7 into the centre of the sequence of the L1 or L2 protein can also be expected, still by a peptide bond; preferably, fragments of E6 or E7 corresponding to remarkable epitopes will be inserted. The insertion into the sequence of the L1 or L2 protein can be carried out while preserving the entire L1 or L2 sequence or alternatively by deleting a portion thereof. Obviously, the construction of appropriate expression cassette (by genetic fusion) coding for these hybrid proteins will preside over the production of these proteins.

As previously mentioned, the component(s) constituting the capsid may be produced in recombinant systems, bacteria, yeast, mammalian or insect cell. For example, WO 95/31476 deals with the expression and purification of an L1 protein in and from *E. coli*. The expression and purification in and from yeast, of the L1 proteins of HPV-6a, -11, -16 and -18 is described in WO 95/31532, as well as the co-expression and the co-purification of these same proteins with the corresponding L2 proteins. The expression of the L1 protein or of the L1 and L2 proteins of type 16, in mammalian cells, with the aid of a vaccine vector, is described in WO 93/2184 and Zhou et al., Virology (1991) 185: 251. The expression of the type 1 L1 protein, in mammalian cells COS, with the aid of the plasmid pSVL is described in WO 94/152 and Ghim et al., Virology (1992) 190 : 548. The expression of the type 1 L1 protein, by means of the vaccine system, is also disclosed by Hagensee et al., J. Virol. (1993) 67: 315. he expression of the type 16 L1 protein and its co-expression with the corresponding L2 protein, in insect cells, with the aid of a baculovirus, is described in WO 94/5792 and Kirnbauer et al., J. Virol. (1993) 67: 6929. On the same subject, Xi et al., J. Gen. Virol. (1991), 72: 2981, may also be mentioned. The expression of the type 11, 16 and 18 L1 protein, in the same system, is reported by WO 94/20137 and Rose et al., J. Virol. (1993) 67: 1936. Thus, the development of a recombinant system intended for the expression of an L1 protein or of the L1 and L2 proteins is clearly within the capability of persons skilled in the art.

When these proteins are produced in a prokaryotic system, they generally remain in the dissociated state after purification. There is no formation of VLPs unless if these proteins are subjected to a specific renaturation treatment, and even in this particular case, the yield remains very low.

When these proteins are expressed in a eukaryotic system, there is generally an expectation for the proteins produced to reassemble spontaneously in the form of VLPs, except for example if the level of expression was too low. Consequently, the product which is obtained after purification is indeed VLPs and not dissociated proteins.

In order to implement the subject of the present invention, the VLPs produced in a eukaryotic system should therefore be treated so as to dissociate them into their components. The dissociation requires that the disulphide bridges are reduced and that the calcium ions are removed (Volpers et al., J. Virol. (1995) 69: 3258 and Colomar et al., J. Virol. (1993) 67: 2779). For example, the VLPs will be placed at alkaline pH or a reducing agent such as dithiothreitol (DTT) will be used. A calcium-complexing chelating agent such as EGTA (ethylene glycol-bis (beta-aminoethyl ether)-N,N,N',N'-tetraacetic acid) will also be used.

For the purposes of the present invention, the nucleic acid encapsulated may be RNA or DNA; the latter will be mainly preferred. The size of the molecule is not critical; it should be stated however that it is preferable that it does not exceed 8 kbp, at least as regards the DNA.

A nucleic acid molecule which is useful for the purposes of the present invention should be different from the papillomavirus genome, although it can contain some components thereof. In particular, this molecule does not have the structure of a papillomavirus genome and does not contain a replication origin specific for a papillomavirus.

The DNA may be in a linear or circular form; the latter form being preferred. Advantageously, it will be a plasmid. The latter will be integrative or not, depending on the desired aim. Likewise, it may or may not replicate in a mammalian cell. For production purposes, it will comprise e.g. a prokaryotic replication origin.

The DNA molecule, e.g. the plasmid, may optionally comprise a site which allows it to bind to the E2 protein of a papillomavirus. Such a site may have as sequence the formula $ACCN_6MT$ in which N is independently A, G, C or T and M is G or T. The DNA molecule may also comprise all or part of the long control region (LCR) of the genome of a papillomavirus.

The essential function of this DNA (or RNA) molecule is to allow the expression of one or more peptides, polypeptides or proteins of interest in a mammalian cell. Consequently, it comprises a coding region placed under the control of an appropriate promoter. By way of example, there may be mentioned the human cytomegalovirus early promoter described in particular in the American Patent U.S. Pat. No. 5,168,062 or a tissue-specific promoter such as the promoter of the gene coding for human desmin (Li et al., Géne (1989) 78: 243 and Li et al., Development (1993) 117: 947).

The choice of the coding region will be determined by the intended use of the VLPs according to the invention. Thus, these VLPs can be used as a vaccination agent against parasitic, bacterial or viral infections. In this case, the peptide or polypeptide or the protein will be selected from parasitic, bacterial or viral antigens.

According to a specific embodiment, the use of the VLPs according to the invention as a therapeutic or preventive vaccination agent against papillomavirus infections is chosen. For this, the peptide(s), polypeptide(s) or protein(s) encoded will be advantageously selected from all or part of the E1 and E2 proteins and nononcogenic forms of the E6 and E7 proteins of a papillomavirus; preferably of a type 16, 18, 31, 33, 35 or 45 HPV. This papillomavirus may be optionally of a type different from the one from which the capsid protein(s) is (are) derived.

The nononcogenic forms include the E6 and E7 proteins of a nononcogenic papillomavirus as well as the deleted forms of an E6 or E7 protein of an oncogenic papillomavirus; advantageously, such a deleted form of an E6 protein does not comprise all or part of the E6 region between amino acid residues 106 and 115 (for example, it may be an HPV-16 E6 Δ (106–110) or Δ (111–115) or Δ (106–115) protein). Likewise, a deleted form of an E7 protein does not comprise all or part of the E7 region between amino acid residues 20 and 26 (for example it may be an HPV-16 E7 Δ (21–24) or Δ (21–26) protein).

These early proteins, their corresponding DNA fragment as well as their nononcogenic form are described in Crook et al., Cell (1991) 67: 547 and Munger et al., EMBO J. (1998) 8: 4099.

By way of example, various possible combinations as regards the origin of the proteins are presented below (nonexhaustive presentation):

| Capsid | | Nucleic acid | |
|---|---|---|---|
| L1 | L2 | E6 | E7 |
| HPV-16 | HPV-16 | HPV-16 | HPV-16 |
| HPV-16 | HPV-16 | HPV-18 | HPV-18 |
| HPV-16 and HPV-18 | HPV-16 | HPV-16 and HPV-18 | HPV-18 and HPV-18 |
| HPV-16 and HPV-18 | — | HPV-33 | — |
| HPV-16 | — | HPV-16 | — |
| HPV-16 | — | — | HPV-16 |

In another aspect, it is also possible to envisage using the VLPs according to the invention as a vaccination agent against tumours induced by autoantigens, preventively or therapeutically. Among the antigens associated with tumours, there may be mentioned in particular tyrosinase, the glycoprotein gp100, the MAGE protein family, CEA, the ras protein, mutated or otherwise, the p53 protein, mutated or otherwise, Muc1 and pSA.

VLPs according to the invention may also be highly useful for delivering in vivo cytokines or secondary molecules having an immunomodulatory function (e.g. cellular recognition by the helper T cells), in all applications where these molecules are prescribed. Among the cytokines, there may be mentioned in particular interleukin-2 (IL-2), IL-4, -5, -7, -10, -12, GM-CSF (granulocyte macrophage colony stimulating factor), gamma interferon (gamma-IFN) and TGF-beta (tumour growth factor-beta). Among the secondary molecules, there may be mentioned in particular B7.1, B7.2, CD40, CD28 and CIITA.

For example, a nucleic acid molecule useful for the purposes of the present invention may not only comprise a region coding for an antigen of an infectious agent or of an autoantigen associated with a tumour, but also a region coding for a cytokine, e.g. IL-2 or IL-12. In order to treat or prevent papillomavirus infections, such a region may be added to the nucleic acid molecule as previously envisaged. In general, this may also be carried out for any other vaccinal application.

Likewise, VLPs according to the invention whose nucleic acid molecule would essentially code for at least one cytokine or at least one secondary molecule can be useful in therapy as a component for treating various pathologies such as tumours or autoimmune diseases or alternatively for preventing a rejection after a transplant.

Finally, VLPs according to the invention may also be useful in the treatment of genetic diseases. In this particular case, for encapsidation, a nucleic acid molecule is prepared which comprises at least one region coding for a protein of interest correcting a genetic defect, such as factor VIII, for treating haemophilia, dystrophin for treating Duchenne's muscular dystrophy (myopathy) or the protein CFTR (cystic fibrosis transmembrane regulator) for treating cystic fibrosis.

Consequently, the subject of the invention is also:
(i) as a medicament, a VLP according to the invention;
(ii) a pharmaceutical composition comprising, as active ingredient, at least one VLP according to the invention in combination with a pharmaceutically acceptable diluent or carrier;
(iii) a pharmaceutical composition comprising at least two VLPs, in which a first VLP comprises a capsid consisting of at least all or part of the L1 protein of a first type, such as type 16 and in which a second VLP comprises a capsid consisting of at least all or part of the L1 protein of a second type different from the first type, such as type 18;
(iv) the use of a VLP according to the invention, in the preparation of a medicament for the prevention or treatment of a bacterial or viral infection, of a tumour i.a. induced by an autoantigen or of an autoimmune disease or alternatively, for the prevention of graft rejection;
(v) a method for the treatment or prevention of a bacterial or viral infection, of a tumour i.a. induced by an autoantigen or of an autoimmune disease or alternatively, for the prevention of graft rejection, according to which a therapeutically or prophylactically effective quantity of at least one VLP according to the invention is administered to an individual needing such a treatment; and
(vi) a method of in vivo expression, which makes it possible to provide a mammal with a peptide, a polypeptide or a protein in a physiologically active form, according to which at least one VLP according to the invention in which the nucleic acid molecule comprises a region coding for the said peptide or polypeptide or for the said protein, placed under the control of an appropriate promoter if a DNA molecule is involved, is administered to the mammal.

A composition according to the invention may be manufactured in a conventional manner. In particular, at least one VLP is combined with a pharmaceutically acceptable diluent or carrier. Examples of diluents or carriers as well as of methods of formulation are indicated in Remington's Pharmaceutical Sciences. The formulation may depend on the route of administration; aerosol, injectable formulation, suppositories, tablets and the like.

A composition according to the invention may be administered by any conventional route in use in the field of vaccines, when this composition is intended to this effect. They are in particular the systemic routes, e.g. subcutaneous, intradermal, intramuscular or intravenous route, and mucosal routes, e.g. oral, nasal, pulmonary or anogenital route. When the treatment of solid tumours is involved, the abovementioned routes continue to be used and the intratumour route may also be added thereto. When the treatment of genetic diseases is involved, the choice of the route of administration will essentially depend on the nature of the disease; for example, there may be advantageously mentioned the pulmonary route in the case of cystic fibrosis (the VLPs being formulated in aerosol form) or the intravenous route in the case of haemophilia.

The administration may be carried out at a single dose or at a dose repeated once or several times after a certain time interval. The appropriate dosage varies according to various parameters, for example the individual treated or the mode of administration. In general, one dose comprises from 1 to 250 $\mu$g of VLPs according to the invention.

The invention also relates to a method of preparing VLPs according to the invention, according to which a nucleic acid molecule as defined above is mixed with all or part of the L1 protein of a papillomavirus in dissociated form and, optionally, all or part of the L2 protein of a papillomavirus, in the presence of an agent allowing the reassociation of the L1 protein (or of the L1 and L2 proteins) in capsid form, e.g. a calcium salt, and the said VLPs are recovered from the mixture.

When the DNA intended to be encapsidated comprises a site which allows it to bind to the E2 protein, it becomes advantageous to add this protein to the reconstitution mixture. This protein would, for example, have been previously produced by the recombinant route, in a prokaryotic (bacteria) or eukaryotic (i.a. yeast, insect cells) system.

Prior to the mixing step, it is advantageous to express all or part of the L1 protein, optionally all or part of the L2 protein, by the recombinant route in a eukaryotic host cell. In this case, the empty virus-like particles are recovered and they are treated with a reducing agent and/or with a calcium-ion chelating agent in order to obtain all or part of the L1 protein, optionally all or part of the L2 protein, in dissociated form.

Advantageously, all or part of the $L_1$ protein, optionally all or part of the $L_2$ protein, is expressed by the recombinant route in insect cells infected with a baculovirus into whose genome a DNA fragment is inserted which codes for all or part of the L1 protein, optionally for all or part of the L2 protein, placed under the control of an appropriate promoter.

When the VLPs according to the invention are used in long-term treatments, such as for example in the treatment of a cancer, the repeated administration of the same type of VLPs (that is to say of VLPs having the same capsid) may be problematic from an immunological point of view. In order to overcome this potential disadvantage, it is possible to envisage the sequential use of VLPs having different capsids. For example, it is possible to prepare a whole range of VLPs having the same nucleic acid molecule (having a region coding e.g. for IL-2 or IL-12) but differing in the type of papillomavirus from which the L1 protein and optionally the E2 protein are derived. Thus, there will be used in succession type 16 capsid VLPs (once or several times), and then type 18 capsid VLPs (once or several times) and the like.

Accordingly, the subject of the invention is also:

(i) a method of treating a genetic disease, a cancerous state or a papillomavirus infection according to which the VLPs according to the invention are repeatedly administered to a mammal needing such a treatment at $t_n$, $t_{n+1}$; n being a number greater than or equal to 1; the VLPs administered at $t_{n+1}$ differing from the VLPs administered at $t_n$ in that the $L_1$ or the $L_1$ and $L_2$ proteins of the capsid of the VLPs administered at $t_{n+1}$, is (are) derived from a papillomavirus of a type other than that from which the $L_1$ protein or the $L_1$ and $L_2$ proteins of the capsid of the VLPs administered at $t_n$ is (are) derived; and (ii) a pharmaceutical composition which comprises several products for administration in succession; the products each consisting of VLPs according to the invention and differing from each other in that the $L_1$ protein or the $L_1$ and $L_2$ proteins of the capsid of the VLPs is (are) derived for each product from a different type of papillomavirus.

EXAMPLE

Preparation of Empty VLPs

A stock of HPV-16 type VLPs is prepared from a culture of Sf-9 cells infected with a recombinant papillomavirus. This baculovirus possesses, inserted into its genome, the DNA fragments of HPV-16 coding for $L_1$ and $L_2$, which were originally isolated from a *condylomata acuminata*. The sequence coding for $L_1$ is disclosed in WO 94/5792. It should be noted in particular that the codon corresponding to the amino acid at position 202 is an aspartic acid codon.

The construction of the baculovirus, the culture of the Sf-9 cells as well as the purification of the VLPs are described in Kirnbauer et al., J. Virol. (1993) 67: 6929 or in Suzich et al., PNAS (1995) 92: 11553.

Dissociation of the VLPs

250 μl of 1 mM phosphate buffer pH 8 containing 300 mM NaCl, 2 mM EGTA (ethylene glycol tetraacetic acid) and 40 mM DTT (dithiotreitol) are added to 250 μl of a preparation of VLPs obtained after dialysis against a 1 mM phosphate buffer pH 8. The incubation is left to continue at 37° C. for one hour. The final concentration of VLPs subjected to dissociation is of the order of 200 μg/ml. A variant of the dissociation protocol is also described in Volpers et al., J. Virol. (1995) 69: 3258. This preparation is then dialysed extensively against 1 mM phosphate buffer pH 8.

Preparation of the DNA Intended to be Encapsidated

The plasmid pnRSV-NP (A/PR/8/34) which comprises the cDNA coding for the nucleoprotein of the influenza virus A/PR/8/34 under the control of the Rous sarcoma virus (RSV) promoter is prepared as described in Ulmer et al., Science (1993) 259: 1745.

Encapsidation of the DNA 50 ng of purified DNA in a volume of 500 μl are added to 500 μl of the preparation of dissociated VLPs obtained above. Next, 25 μl of a 20 mM calcium chloride solution are added. The mixture is incubated for 30 min at 37° C. It is then subjected to centrifugation in 40% sucrose in an SW28 rotor at 28,000 rpm for 20 hours. A band is recovered at the density of 1.33 g/ml which contains the encapsidated DNA and which is dialysed against 1 mM phosphate buffer pH 8.

What is claimed is:

1. A noninfectious virus-like particle (VLP) which comprises:

(i) a capsid defining an internal space and consisting of at least a portion of the $L_1$ protein of a papillomavirus that has the ability to self-assemble into a VLP, and (ii) a nucleic acid molecule contained in the said internal space; the nucleic acid molecule being different from the genome of a papillomavirus at least in that it lacks all or part of the regions of the said genome coding for wild-type late proteins.

2. The virus-like particle according to claim 1, in which the capsid consists of said at least a portion of the $L_1$ protein in the $L_1$-$E_7$ chimeric protein state.

3. The virus-like particle according to claim 1, in which the capsid consists of said at least a portion of the $L_1$ protein of a human papillomavirus (HPV).

4. The virus-like particle according to claim 3, in which the capsid consists of said at least a portion of the $L_1$ protein of a type 1, 6, 10, 11, 16, 18, 31, 33, 35 or 45 human papillomavirus.

5. The virus-like particle according to claim 4, in which the capsid consists of said at least a portion of the $L_1$ protein of an HPV-16, -18, -31, -33, -35 or -45 initially isolated from a benign lesion.

6. The virus-like particle according to claim 5, in which the capsid consists of said at least a portion of the $L_1$ protein of an HPV-16 having an amino acid sequence which comprises at position 202 an amino acid other than histidine.

7. The virus-like particle according to claim 6, in which the capsid consists of said at least a portion of the $L_1$ protein of an HPV-16 having an amino acid sequence which comprises at position 202 an aspartic acid or glutamic acid residue.

8. The virus-like particle according to claim 5, wherein said benign lesion is condyloma acuminatum or cervical dysplasia.

9. The virus-like particle according to claim 1, in which the capsid, in addition, consists of at least a portion of the $L_2$ protein of a papillomavirus that has the ability to self assemble into a VLP.

10. The virus-like particle according to claim 9, in which the capsid in addition, consists of said at least a portion of the $L_2$ protein in the $L_2$-E7 chimera state.

11. The virus-like particle according to claim 1, in which the nucleic acid molecule comprises a region coding for a protein of interest.

12. The virus-like particle according to claim 11, in which the nucleic acid molecule is DNA and comprises a region coding for a protein of interest placed under the control of a promoter which promotes transcription in mammalian cells.

13. The virus-like particle according to claim 12, in which the DNA molecule comprises, in addition, a papillomavirus $E_2$ protein binding site of formula $ACCN_6MT$ in which N is A, G, C or T and M is G or T.

14. The virus-like particle according to claim 12, in which the DNA molecule comprises, in addition, all or part of the long control region (LCR) of the genome of a papillomavirus.

15. The virus-like particle according to claim 11, in which the nucleic acid molecule is at most 8 kbp.

16. The virus-like particle according to claim 11, in which the nucleic acid molecule comprises at least one region coding for a protein of interest selected from cytokines and secondary molecules facilitating cellular recognition by the helper T cells.

17. The virus-like particle according to claim 11, in which the nucleic acid molecule comprises at least one region coding for a protein of interest selected from tumour-associated antigens.

18. The virus-like particle according to claim 11, in which the nucleic acid molecule comprises at least one region coding for a protein of interest selected from parasitic, bacterial or viral antigens.

19. The virus-like particle according to claim 18, in which the nucleic acid molecule comprises at least one region coding for a protein of interest selected from the $E_1$ and $E_2$ proteins and the nononcogenic forms of the $E_6$ and $E_7$ proteins of a papillomavirus.

20. The virus-like particle according to claim 19, in which the nucleic acid molecule comprises at least one region coding for a protein of interest selected from the $E_1$ and $E_2$ proteins and the nononcogenic forms of the $E_6$ and $E_7$ proteins of a papillomavirus of the HPV-16, -18, -31, -33, -35 or -45 type.

21. The virus-like particle according to claim 19 or 20, in which the nucleic acid molecule comprises at least one region coding for a protein of interest selected from the $E_1$ and $E_2$ proteins and the nononcogenic forms of the $E_6$ and $E_7$ proteins of a papillomavirus of a type different from the one from which the capsid protein or protines are derived.

22. The virus-like particle according claim 10, in which the nucleic acid molecule comprises at least one region coding for a protein of interest in the therapy of genetic diseases.

23. A virus-like particle as a medicament according to claim 1.

24. A method of preparing virus-like particles according to claim 1, wherein a nucleic acid molecule different from the genome of a papillomavirus at least in that it lacks all or part of the regions of the said genome coding for the wild-type late proteins is mixed with said at least a portion of the $L_1$ protein of a papillomavirus in dissociated form, in the presence of a calcium salt and the said virus-like particles are recovered from the mixture.

25. The method of preparation according to claim 24, wherein all or part of the $E_2$ protein of a papillomavirus is mixed with the nucleic acid molecule and with the $L_1$ protein.

26. The method of preparation according to claim 25, wherein the papillomavirus $E_2$ protein deleted for its N-terminal part is added at the time of mixing.

27. The method of preparation according to claim 24, wherein prior to the mixing step, (i) said at least a portion of the $L_1$ protein is expressed by the recombinant routes (ii) the empty virus-like particles are recovered and (iii) the empty virus-like particles are treated with a reducing agent and/or with a calcium-ion chelating agent in order to obtain said $L_1$ protein in dissociated form.

28. The method of preparation according to claim 27, in which said at least a portion of the $L_1$ protein is expressed by the recombinant route in insect cells infected with a baculovirus into whose genome a DNA fragment is inserted which codes for said $L_1$ protein placed under the control of an appropriate promoter.

29. The method of preparation according to claim 28, wherein said preparation further comprises at least a portion of the $L_2$ protein that has the ability to self assemble into a VLP to be expressed by the recombinant route in insect cells infected with a baculovirus into whose genome a DNA fragment is inserted which codes for said $L_2$ protein placed under the control of an appropriate promoter.

30. The method of preparation according to claim 27, wherein step (i) further comprises at least a portion of the $L_2$ protein that has the ability to self assemble into a VLP to be expressed by the recombinant route and wherein step (iii) further comprises said $L_2$ protein in dissociated form.

* * * * *